United States Patent [19]

Gutierrez et al.

[11] 4,022,803

[45] May 10, 1977

[54] PROCESS FOR PREPARING ISOCITRIC ACID, ALLOISOCITRIC ACID AND LACTONES THEREOF

[75] Inventors: Eddie N. Gutierrez, Fort Lee; Vincent Lamberti, Upper Saddle River, both of N.J.

[73] Assignee: Lever Brothers Company, New York, N.Y.

[22] Filed: Dec. 22, 1975

[21] Appl. No.: 642,839

[52] U.S. Cl. .................. 260/343.6; 260/535 R; 260/485 H
[51] Int. Cl.$^2$ ............. C07D 307/32; C07C 51/09
[58] Field of Search .................. 260/343.6, 535 P

[56] References Cited

OTHER PUBLICATIONS

Gawron, et al., JACS 80: 5856 (1958).

Pucher, et al., J. Biol. Chem. 163: 169–184 (1946).

*Primary Examiner*—Cecilia M. S. Jaisle
*Attorney, Agent, or Firm*—James J. Farrell; Kenneth F. Dusyn; Melvin H. Kurtz

[57] ABSTRACT

Novel methods for preparing polycarboxylic compounds which are useful as metal sequestrants and food acidulants are disclosed. These compounds, isocitric acid, alloisocitric acid and lactones thereof, can also be neutralized to the corresponding salts, which in turn are metal sequestering agents. The novel methods for the preparation of these compounds include halogenation of propane 1,1,2,3-tetracarboxylic acid or its salts and/or the tetraester of the acid with subsequent formation of isocitric acid, alloisocitric acid and their lactones under specified pH conditions.

14 Claims, No Drawings

PROCESS FOR PREPARING ISOCITRIC ACID, ALLOISOCITRIC ACID AND LACTONES THEREOF

This invention broadly relates to novel processes for the preparation of certain tricarboxylic acids and lactones thereof. These compounds, while useful in themselves as metal sequestering agents, may also be neutralized to form the salts corresponding to the particular compound employed. These salts in turn are metal sequestering agents and/or detergent builders. The acid forms of the compounds, i.e. isocitric acid, alloisocitric acid and their lactones, are also useful as food acidulants.

The prior art methods of preparing alloisocitric acid, isocitric acid, and their lactones are practically limited to natural fermentation, see for example U.S. Pat. No. 2,949,404. Although some synthetic methods have been proposed in the literature such as in the articles by Gawron et al, JACS 80 page 5856 (1958) entitled "Synthetic Evidence for the Stereochemistry of Isocitric Acid and Alloisocitric Acid, Mechanism of cis-Aconitase Action" and that by Pucher and Vickery, J. Biol. Chem. 163 169–184 (1946), none of these methods appear to have been commercialized.

Accordingly, an object of the present invention is to provide a synthetic process for producing isocitric acid, alloisocitric acid and lactones thereof by halogenation and hydrolysis of tetraesters of propane 1,1,2,3-tetracarboxylic acid or saponification of the tetraester followed by halogenation of the salt or acid form depending on the pH conditions and further treatment with mineral acid.

A further object of the invention is to produce isocitric acid, alloisocitric acid and lactones thereof by a process which lends itself to commercial application.

Other objects and advantages will appear as the description proceeds.

The attainment of the above objects is made possible by this invention which includes 1. halogenating a 1,1,2,3-propane tetracarboxylic compound having the general Formula I

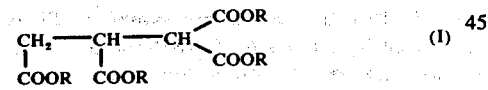

wherein R is independently methyl and/or ethyl to form a halogenated tetracarboxylic compound and then hydrolyzing this halogenated compound at a pH of about 2 or less, preferably by heating with a non-oxidizing mineral acid, for example, by refluxing, to form the mixture of isocitric acid, alloisocitric acid, and lactones thereof, or 2. saponifying a 1,1,2,3 propane tetracarboxylic tetraester of Formula I to form the tetra alkali metal salt by saponification (which can then be acidified to form the acid) and then halogenating either the acid or salt form at a pH below about 8, preferably between 5 and 7, followed by acidification, if required, to a pH of about 1 to form the mixture of isocitric acid, alloisocitric acid, and lactones thereof.

The subject invention, encompassing a novel synthetic process for the preparation of isocitric acid, alloisocitric acid and lactones of these acids, overcomes one or more of the disadvantages of the prior art heretofore described. This is accomplished with the advantage that the compounds may be easily prepared in good yields.

The invention is hereinafter set forth in more detail, specific features thereof being particularly delineated in the appended claims.

In the practice of the present invention, a tetraester of Formula I above is prepared. These tetraester compounds are known and can be prepared by a conventional Michael reaction as set forth in Chapter 3, Volume 10 of the publication entitled "Organic Reactions", edited by Roger Adams etal and published in 1959 by John Wiley & Sons, Inc. These tetraesters of Formula I are treated by either of two methods as follows:

1. The ester is halogenated at a pH of about 2 to about 8 and the resulting product is separated from the reaction mixture. The separated product of Formula II

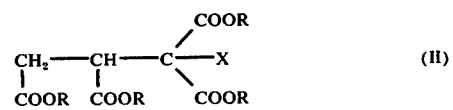

wherein X is chlorine or bromine and R is as previously defined is then hydrolyzed in dilute mineral acid to form a reaction mixture of the desired product as follows:

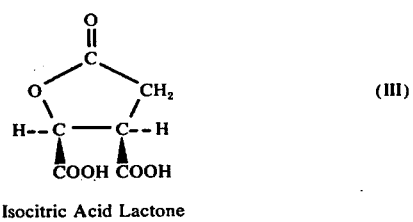

Isocitric Acid Lactone

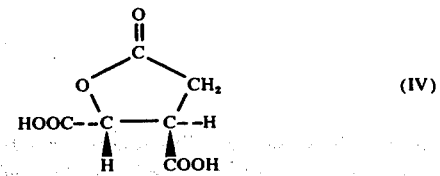

Alloisocitric Acid Lactone

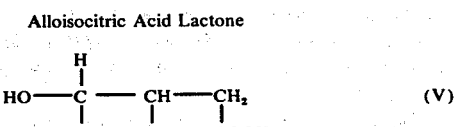

Isocitric Acid

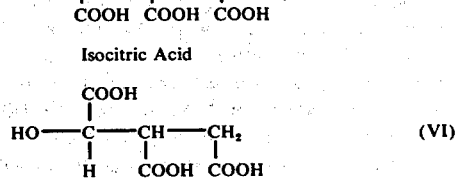

Alloisocitric Acid

2. The ester of Formula I is converted to the salt or acid form by standard saponification and acidification techniques. The resulting tetrasalt or tetraacid has the following Formula VII:

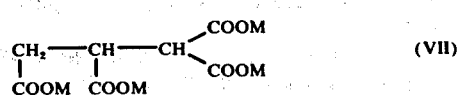

wherein M is hydrogen or an alkali metal and preferably sodium, potassium or lithium. In addition, depending on the pH, mono, di, tri or tetra alkali metal salts of the acid may be present. In these salts M may represent hydrogen as well as alkali metal. At the higher pH levels the compound will be mostly in the tetra alkali metal salt form whereas the lower pH the tetraacid form will be present. The reaction mixture containing the compounds of Formula VII is then halogenated and acidified to form a reaction mixture of the desired products of Formulas III, IV, V and VI. In both methods the racemic forms, i.e. d,l, of the products are obtained.

The desired reaction products are soluble in the reaction mixture and can be readily recovered by conventional methods, such as, for example, by evaporation of the reaction mixture and extraction of the residue with a suitable solvent such as acetone. Distillation of the acetone then leaves the desired products. Recovery of the reaction products may also be accomplished by direct extraction of the reaction mixture with a suitable solvent such as n-butanol, 2-butanol, methyl acetate, ethyl acetate, butyl acetate, isobutyl acetate, and dibutyl ether. The recovered product is sufficiently pure for use as a metal sequestrant or for conversion to the corresponding alkali metal salt for use as a detergent builder. The desired product may be obtained in purer form by well known techniques for purifying isocitric acid.

The present invention permits the synthesis of the desired compounds of Formulas III, IV, V and VI; further, under most conditions these compounds are produced in good yields. An additional advantage of this invention is that the novel synthesis or process produces products in readily recoverable form.

Generally, the reaction of the above-described compounds of Formulas I and VII to produce the compounds of Formulas III, IV, V and VI proceeds as in the reaction diagram of Table I following:

TABLE I

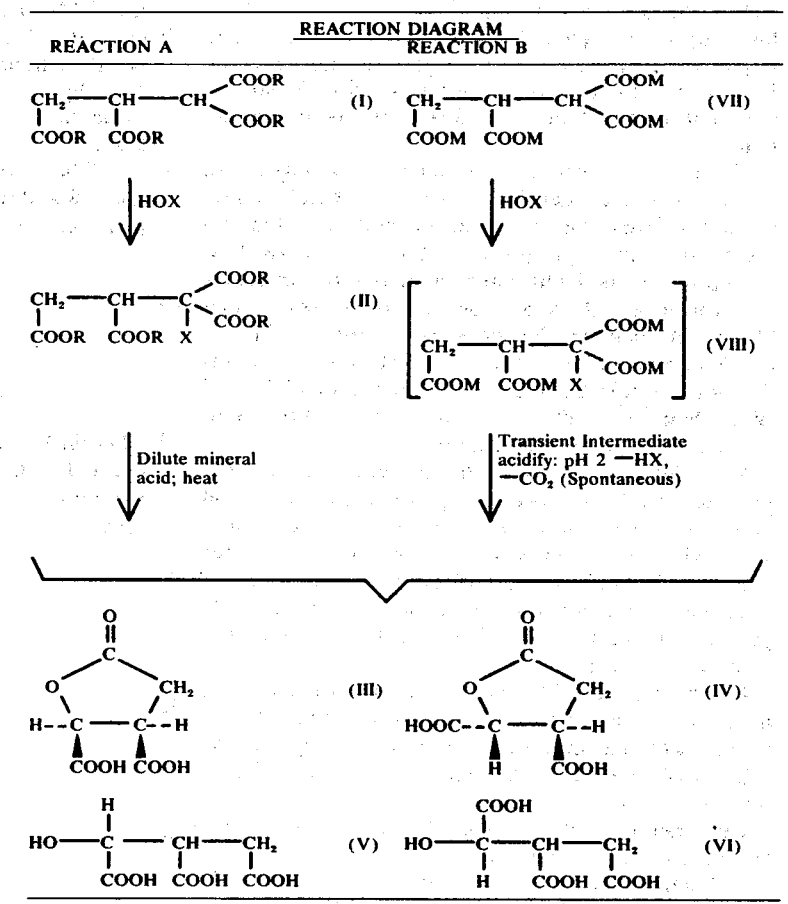

In Reaction A the compound of Formula I is produced by known methods particularly by the Michael reaction as mentioned previously.

The compound of Formula I, as outlined in Reaction A, is halogenated to form a compound of Formula II. The halogenation or reaction medium is preferably one in which the Formula I compound dissolves to facilitate a homogeneous reaction. However, the medium may be either water in which case the compound is dispersed or a cosolvent/water mixture in which the solvent preferably is miscible with the water and serves to dissolve the Formula I compound. Methanol is the cosolvent of choice; however, other solvents such as acetic acid, dimethyl formamide and ethylene glycol which are miscible with water may also be used so long as they do not either excessively react with a hypohalous acid or interfere with the reaction between a hypohalous acid and the compound of Formula I. Alternatively, the reaction may be carried out in the absence of water by utilizing an oranic hypohalite such as tertiary butyl hypochlorite. In this case the reaction preferably is carried out in the presence of an organic liquid which is compatible with and preferably dissolves the organic hypohalite and the compound of Formula I. This organic liquid is suitably a lower alcohol such as methanol, butanol, isobutanol, t-butanol and halogenated hydrocarbons such as carbon tetrachloride.

When the reaction medium contains water it must contain sufficient water to promote formation of the hypohalous acid. This water may be introduced as part of a hypohalous acid solution to be added or may be already present in the reaction mixture which can then be treated with either chlorine or bromine. Thus, the reaction medium may be all water or all cosolvent or any mixture of these. The total amount of reaction medium must be enough to effectively disperse or dissolve the reactants. The ratio of the compound of Formula I to the total amount of reaction medium is generally about 1 mole of the compound to about 200 cc of reaction medium. After introduction of the compound of Formula I into the reaction medium, a solution of a compound.

In the alternative, in the case of a compound of Formula VII which is obtained as an aqueous solution, a cosolvent such as methanol, acetic acid, dimethyl formamide and ethylene glycol, may be added before proceeding with the halogenation.

In the hypohalous acid HOX, X represents chlorine or bromine and thus, for example, an acidified solution of sodium hypochlorite or sodium hypobromite or bromine or chlorine dissolved in water will generate HOX to accomplish the above halogenation. Generally, any alkali metal or alkaline earth metal hypochlorite under acidic conditions may also be utilized but the sodium salts, being readily available, are preferred. The solution of sodium hypochlorite or sodium hypobromite may be of any convenient concentration but dilute solution of about 5% to 15% by weight are readily available and are preferred. The amount of HOX required is about 1 to about 1.1 moles per mole of the compound of Formula I or VII. If a substantially greater ratio of HOX than 1.1 moles per mole of the compound of Formula I or VII is utilized, it will not affect formation of the product but is uneconomical. If substantially less than one mole is employed, the reaction will not proceed to completion. If sodium hypochlorite or sodium hypobromite is used, then a concurrent addition of a non-oxidizing mineral acid such as for example hydrochloric acid is employed to maintain a pH of less than about 8, preferably about 5 to about 7. If bromine or chlorine water is used, the pH of the reaction mixture is maintained below about 8, preferably about 5 to about 7, by the addition of alkali metal carbonates or hydroxides. The above pH range is used to maintain reasonable reaction rates.

The temperature of the above described halogenation is usually about 0° to 50° C to avoid premature decarboxylation prior to halogenation of the compound and to minimize loss of halogen which is in equilibrium in solution with the hypohalous acid. Ambient temperatures are preferred as a matter of practicality and to keep side reactions to a minimum.

In Reaction Scheme A of Table I, after addition of the reactants, the reaction may be monitored by periodic sampling and NMR analysis since the characteristic NMR frequency of the methylene protons will shift from high field in the case of the compound of Formula I to a lower field as the halogenated compound of Formula II is obtained in the reaction medium. The desired amount of halogenated compound of Formula II may be isolated by conventional methods such as extraction. However, since the invention deals with a further reaction of this compound to produce a mixture of products of Formula III, IV, V and VI, the reaction mixture containing the compound II is preferably retained. If required, mineral acid is then added with stirring to this reaction mixture in an amount sufficient to produce a pH of less than about 2 to facilitate hydrolysis of the compound of Formula II. The temperature utilized in this hydrolysis is about 25° C to about 110° C. The hydrolysis is preferably accomplished at a pH of about 1 to 1.5 and a high temperature such as at reflux. The reaction will still proceed, although more slowly, at lower temperatures. To complete the reaction, the total mixture is refluxed for about 1 to about 16 hours, preferably about 6 to about 10 hours. Periodic sampling with NMR analysis also may be used to monitor the reaction.

The ratio of water to halogenated tetraester in the hydrolysis step is not critical but it is convenient to operate in a range of about 3 parts by weight of water to 1 part by weight of the halogenated tetraester of Formula II to about 30 parts by weight of water to about 1 part by weight of halogenated tetraester. After hydrolysis is complete, the reaction mixture is evaporated to remove water and other volatile components and the residue is extracted by conventional procedures such as acetone extraction. The extracting solvent is removed by evaporation leaving the desired products in good yield. Alternatively, after the reflux period is complete, the product, consisting of mainly isocitric acid, alloisocitric acid and the lactones thereof, may be extracted directly from the reaction mixture with a suitable organic solvent such as n-butanol, 2-butanol, methyl acetate, n-ethyl acetate, n-butyl acetate, isobutylacetate and dibutyl ether. The product is then isolated by evaporation of the organic solvent.

In Reaction B of Table I, the compound of Formula VII may be obtained by conventional saponification of the tetraester compound of Formula I followed by acidification to a pH of about 8 or less. If desired, additional water and/or a cosolvent such as methanol, acetic acid, dimethyl formamide and ethylene glycol may be added before proceeding with the halogenation step.

The halogenation procedures operable for Reaction B are exactly the same as those described previously for Reaction A. In Reaction B, however, there is formed a transient intermediate halogenated tetraacid species of Formula VIII which spontaneously decarboxylates and "dehydrohalogenates" as shown in Reaction Scheme B above to form the desired products. After halogenation, the mixture is acidified to a PH of less than about 2 to insure completion of the decarboxylation and lactonization. Further, unlike the procedure of Reaction A no reflux is necessary to form the desired product mixture of the compounds of Formulas III, IV, V and VI. Recovery of the desired products is accomplished in exactly the same manner as in Reaction A.

The following Examples will more fully illustrate the embodiments of this invention. All parts and proportions referred to herein and in the appended claims are by weight unless otherwise indicated.

EXAMPLE I

PREPARATION OF ISOCITRIC AND ALLOISOCITRIC ACIDS AND THEIR LACTONES

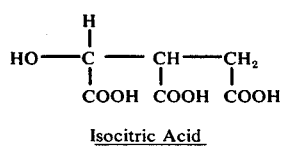
Isocitric Acid

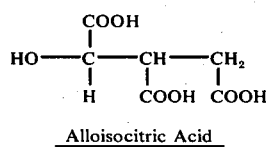
Alloisocitric Acid

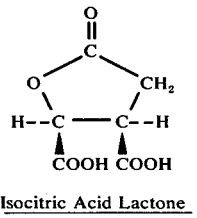
Isocitric Acid Lactone

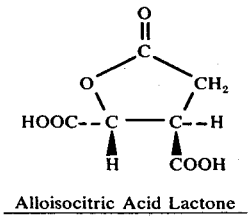
Alloisocitric Acid Lactone

A. PREPARATION OF TETRAMETHYL PROPANE-1,1,2,3-TETRACARBOXYLATE ACID

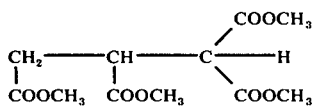

To 200 ml of methanol is added 0.1 gram of sodium metal. After the reaction is complete, 0.1 mole of dimethyl malonate is added. Next, 0.1 mole of dimethyl maleate is added and the resulting solution is refluxed for 4 hours. The reaction mixture is then distilled to yield the tetraester product: b.p. 146°–150° C (2.0–3.0 mm Hg). The structure is confirmed by NMR analysis.

B. PREPARATION OF TETRAMETHYL PROPANE-1-CHLORO-1,1,2,3-TETRACARBOXYLATE

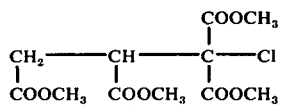

27 grams of the product prepared in I-A above is dissolved in 200 ml of 1:1 methanol:water. 240 grams of sodium hypochlorite solution (5.2% by weight) is slowly added over a 1-hour period while maintaining the pH at 3 to 7 by concurrent addition of dilute HCL (5%). The reaction mixture is evaporated to a syrup, which is then extracted with ether and the ether layer evaporated. The ethereal residue is distilled to give 26 grams (84% of theoretical yield) of product: b.p. 120°–130° C (0.15 mm Hg) and m.p. 43.5°–49.3° C. The structure is confirmed by NMR analysis (in CDCl$_3$).

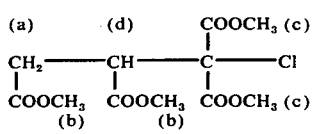

CH$_2$(a) ABX multiplet, 2.80–3.00δ
CH$_3$(b) singlet, 3.70δ
CH$_3$(c) singlet, 3.84δ
CH(d) multiplet, 4.00–4.27δ

C. PREPARATION OF ISOCITRIC ACID AND ALLOISOCITRIC ACIDS AND THEIR LACTONES 200 grams of the product prepared in I-B above is placed into 1000 ml H$_2$O containing 100 g. conc. HCl and the mixture is refluxed for 12 hours. The solution is evaporated to dryness to leave 128 grams of products containing 60.7% of a mixture of the compounds of Formulas III, IV, V and VI, with III and IV in predominance.

EXAMPLE II

A. PREPARATION OF TETRAMETHYL PROPANE-1-BROMO-1,1,2,3-TETRACARBOXYLATE

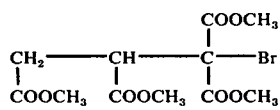

13.8 g. (0.05 mole) of the product prepared in Example I-A above is mixed with 200 mls. of water in a reaction vessel. Bromine, 22 g. (0.1 mole) is added dropwise over a two-hour period while maintaining the pH at 5–6 by the simultaneous addition of Na$_2$CO$_3$. The reaction mixture is then extracted with ether and the ether extract evaporated in vacuo to give 14.8 g. (98% of theoretical yield) of tetramethyl propane-1-bromo-1,1,2,3-tetracarboxylate. The structure is confirmed by NMR analysis (in CDCl$_3$):

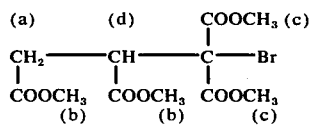

CH$_2$(a) ABX doublet, centered at 2.89δ
CH$_3$(b) singlet, 3.78δ
CH$_3$(c) singlet, 3.81δ
CH(d) multiplet, centered at 3.99δ

B. PREPARATION OF ISOCITRIC ACID, ALLOISOCITRIC ACID AND THEIR LACTONES 35.5 grams of the product prepared in Example II-A is mixed with 250 mls. water and 100 mls. of concentrated hydrochloric acid. The solution is refluxed for 10 hours and then evaporated to dryness in vacuo.

10 grams of product is obtained consisting of 79.4% isocitric acid, alloisocitric acid and their lactones as determined by NMR analysis (D$_2$O). The lactones predominate in the mixture.

EXAMPLE III

PREPARATION OF ISOCITRIC ACID, ALLOISOCITRIC ACID AND THEIR LACTONES

A. PREPARATION OF PROPANE-1,1,2,3-TETRACARBOXYLIC ACID

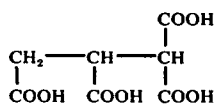

Tetramethyl propane-1,1,2,3-tetracarboxylate, 160 g. (0.6 mole) prepared as in I-A is dissolved in a mixture of 100 ml methanol and 300 g. water. Two hundred grams of 50% NaOH is added slowly over a two-hour period. The resulting mixture is refluxed for 6 hours, cooled to 15° C and acidified with 500 g. of cold 20% hydrochloric acid. The solution is then evaporated in vacuo. The residue is taken up in acetone, filtered to remove inorganic salts and the acetone filtrate evaporated in vacuo to give 130 g. of propane-1,1,2,3-tetracarboxylic acid. The structure is confirmed by NMR analysis (in acetone-d-6).

B. Propane-1,1,2,3-tetracarboxylic acid, 11 g. (0.05 mole) prepared as in Example III-A above, is dissolved in 200 mls. of water and neutralized to a pH of 7.5 with $Na_2CO_3$. One hundred grams of 5.2% sodium hypochlorite solution is added dropwise while maintaining the pH of the reaction mixture at 7.5 by the simultaneous addition of dilute hydrochloric acid. The reaction mixture is then acidified to a pH of 1.3 with additional hydrochloric acid and evapored in vacuo to give a solid residue. The residue is then taken up in acetone and filtered to remove inorganic salts. The acetone filtrate is evaporated in vacuo to give 8 g. of a residue. NMR analysis ($D_2O$) shows the residue to consist predominately of a 1:1 mixture of the lactone of isocitric acid to the lactone of alloisocitric acid. This residue additionally contains a small amount of isocitric acid and alloisocitric acid.

C. Propane-1,1,2,3-tetracarboxylic acid; 11 g. (0.05 mole), is dissolved in 200 ml of water and neutralized to pH 6.0 with sodium carbonate. Bromine, 10 g. (0.06 mole), is added dropwise while maintaining the pH of the reaction mixture at 6 by the simultaneous addition of sodium carbonate. The reaction mixture is then acidified to pH 1.3 with dilute hydrochloric acid and evaporated in vacuo to give a solid residue. The residue is then taken up in acetone and filtered to remove inorganic salts. The acetone filtrate is evaporated in vacuo to give 8 g. of a residue. NMR analysis ($D_2O$) shows the residue to consist predominantly of a 1:1 mixture of isocitric acid and its lactone:alloisocitric acid and its lactone, wherein the lactone forms predominate as in III-B above.

This invention has been described with respect to certain preferred embodients, and various modifications and variations in the light thereof will be suggested to persons skilled in the art and are to be included within the spirit and purview of this application and the scope of the appended claims.

What is claimed is:

1. A process for preparing a mixture of isocitric acid, alloisocitric acid and gamma lactones of isocitric acid and alloisocitric acid comprising halogenating a tetraester compound of the formula

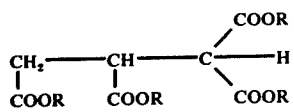

wherein R independently represents methyl and/or ethyl, in an aqueous medium, with a hypohalous acid selected from the group consisting of hypochlorous acid and hypobromous acid to form a halogenated tetraester of the formula

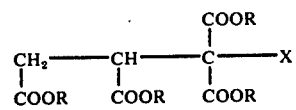

wherein X represents chlorine or bromine and said R is as previously defined; and hydrolyzing said halogenated tetraester in an aqueous medium with a non-oxidizing mineral acid to form said mixture.

2. A process as defined in claim 1 wherein said halogenation takes place at a pH of less than about 8 and at a temperature of about 0° C to about 50° C.

3. A process as defined in claim 1 wherein said hypohalous acid is hypochlorous acid.

4. A process as defined in claim 1 wherein said hydrolysis takes place at a pH of less than about 2 and at a temperature of about 25° C to about 110° C.

5. A process as defined in claim 1 wherein said aqueous medium is water or a mixture of water with a cosolvent selected from the group consisting of methanol, ethylene glycol, acetic acid, dimethyl formamide and mixtures thereof.

6. A process as defined in claim 1 wherein said R is methyl.

7. A process as defined in claim 1 wherein said R is ethyl.

8. A process for preparing a mixture of isocitric acid, alloisocitric acid and gamma lactones of isocitric acid and alloisocitric acid comprising halogenating a compound of the formula

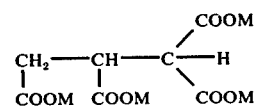

wherein M independently represents hydrogen or an alkali metal cation selected from the group consisting of sodium, potassium and lithium in an aqueous medium with a hypohalous acid selected from the group consisting of hypochlorous acid and hypobromous acid to form a transient halogenated species of the formula

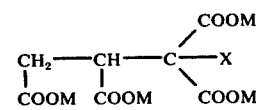

wherein X represents chlorine or bromine and said M is as previously defined; said transient species spontaneously decarboxylating and dehydrohalogenating under the conditions of halogenation to form said mixture.

9. A process as defined in claim 8 further comprising adjusting the pH of said aqueous medium to less than about 2 after said halogenating to insure completion of said decarboxylation and dehydrohalogenation.

10. A process as defined in claim 8 wherein said halogenation takes place at a pH of less than about 8 and at a temperature of about 0° C to about 50° C.

11. A process as defined in claim 8 wherein said hypohalous acid is hypochlorous acid.

12. A process as defined in claim 8 wherein said hydrolysis takes place at a pH of less than about 2 and at a temperature of about 25° C to about 110° C.

13. A process as defined in claim 8 wherein said M is hydrogen.

14. A process as defined in claim 10 wherein at least one of said M is sodium.

* * * * *